(12) United States Patent
Birkill et al.

(10) Patent No.: US 12,420,095 B2
(45) Date of Patent: Sep. 23, 2025

(54) EARPIECE WITH ELECTRODES

(71) Applicant: ALGIAMED LTD, Ebene (MU)

(72) Inventors: Corlius Birkill, Pretoria (ZA); Lourend Carl Lurock Höll, Pretoria (ZA); Tyrone Donovan Patrick, Pretoria (ZA); Francesca Marsili, Montecosaro (IT); Barend Jacques Swart, Bryanston (ZA); Renaldo Goosen, Pretoria (ZA)

(73) Assignee: ALGIAMED LTD, Ebene (MU)

( * ) Notice: Subject to any disclaimer, the term of this patent is extended or adjusted under 35 U.S.C. 154(b) by 193 days.

(21) Appl. No.: 18/371,164

(22) Filed: Sep. 21, 2023

(65) Prior Publication Data

US 2024/0091535 A1   Mar. 21, 2024

Related U.S. Application Data

(60) Provisional application No. 63/408,643, filed on Sep. 21, 2022.

(51) Int. Cl.
*A61N 1/36* (2006.01)
*A61N 1/04* (2006.01)

(52) U.S. Cl.
CPC ....... *A61N 1/36036* (2017.08); *A61N 1/0456* (2013.01)

(58) Field of Classification Search
None
See application file for complete search history.

(56) References Cited

U.S. PATENT DOCUMENTS

| | | | |
|---|---|---|---|
| 2015/0018926 A1* | 1/2015 | Frenkel | A61N 1/0472 607/139 |
| 2015/0360030 A1* | 12/2015 | Cartledge | A61N 1/3603 607/136 |
| 2022/0040480 A1* | 2/2022 | Bouton | A61N 1/36014 |
| 2023/0233855 A1* | 7/2023 | Sunkeri | A61N 1/36036 607/55 |

FOREIGN PATENT DOCUMENTS

| | | | | |
|---|---|---|---|---|
| WO | WO-2012156052 A2 | * | 11/2012 | ......... A61H 39/002 |
| WO | WO-2020198453 A1 | * | 10/2020 | |

* cited by examiner

*Primary Examiner* — Qin Zhu
(74) *Attorney, Agent, or Firm* — Amster, Rothstein & Ebenstein LLP (57) ABSTRACT

An earpiece including a frame with an over ear portion and a lower portion including an upper arm including at least a first electrode and a lower arm including at least a second electrode, wherein the upper arm and the lower arm are flexible and resilient to mount the earpiece in a user's ear.

19 Claims, 11 Drawing Sheets

EARPIECE WITH ELECTRODES

CROSS-REFERENCE TO RELATED APPLICATIONS

The present application claims benefit of and priority to U.S. Provisional Patent Application Ser. No. 63/408,643 filed Sep. 21, 2022, and entitled EARPIECE WITH ELECTRODES, the entire contents of which are hereby incorporated by reference herein.

BACKGROUND

Field of the Disclosure

The present invention relates to an earpiece including electrodes configured and positioned for stimulation of the vagus nerve when in place in a user's ear. In particular, the earpiece includes a pair of flexible arms including the electrodes that may be flexed to position the electrodes appropriately with respect to the vagus nerve.

Related Art

The "vagus nerve" is a term that conventionally refers to two very long nerves, a left and a right, that extend from the brain down through the neck, chest and abdomen and carry both motor and sensory information to a number of parts of the body. The vagus nerve provides information to and carries information from the muscles of the throat as well as the voice box. In addition, the vagus nerve is responsible for regulation of heart rate as well as the gastrointestinal system. The vagus nerve also carries sensory information from a variety of organs throughout the body. In addition, the vagus nerve serves as the primary nerve of the parasympathetic nervous system.

Figure 1:
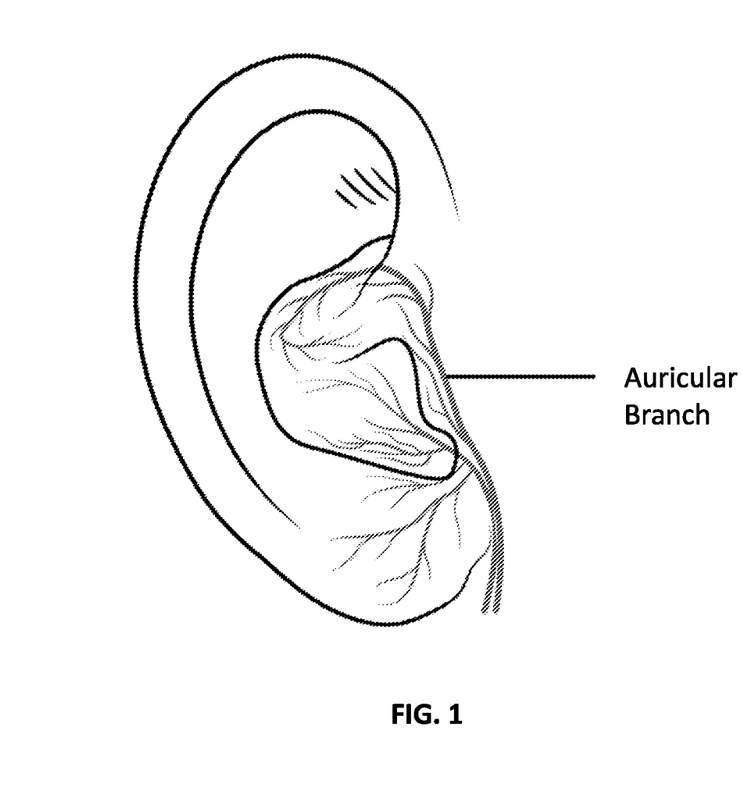
FIG. 1 is an exemplary illustration of the auricular branch of the vagus nerve in a user's ear.
Figure 2:
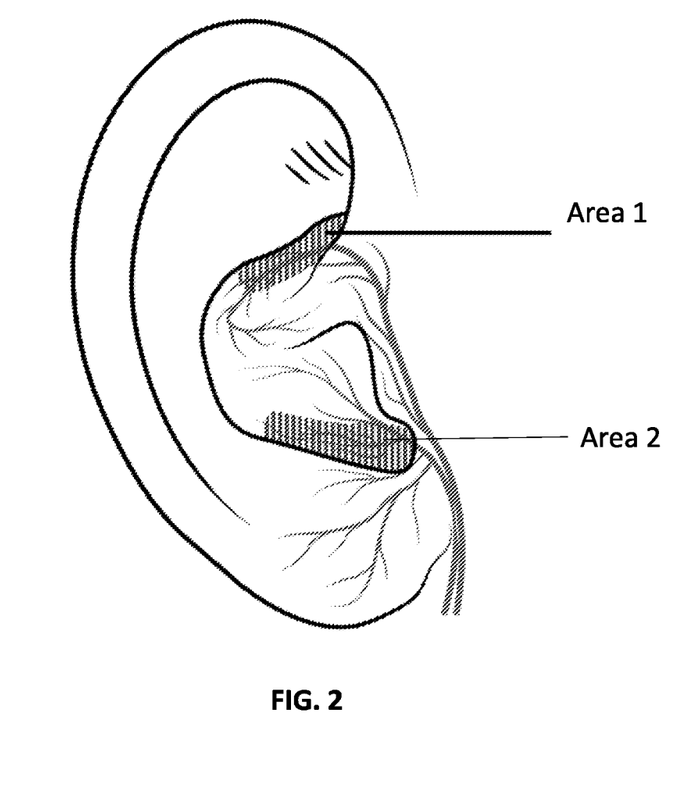
FIG. 2 is an exemplary illustration of a user's ear highlighting the areas thereof that are suitable for stimulating the auricular branch of the vagus nerve.
Figure 3:
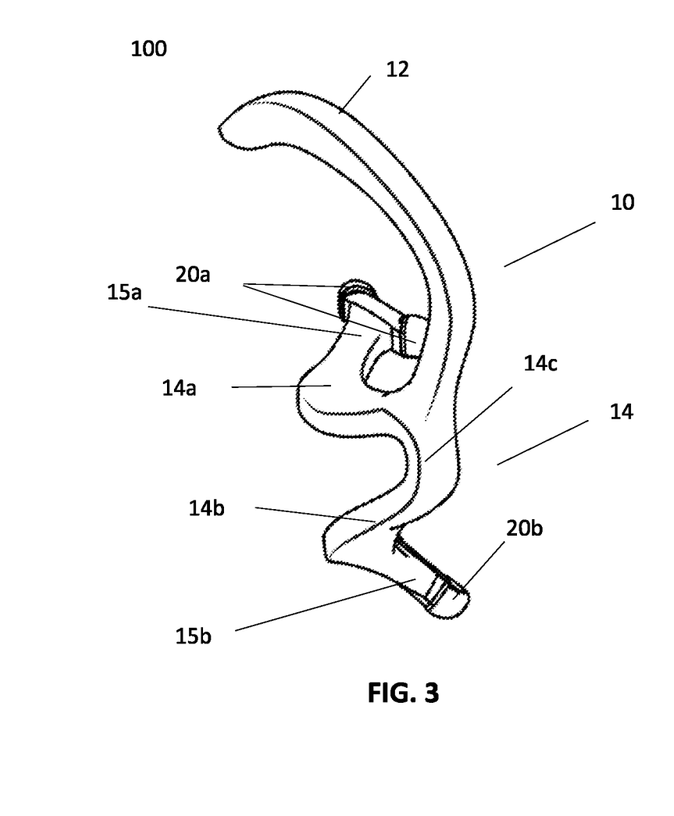
FIG. 3 illustrates a perspective view of an earpiece in accordance with an embodiment of the present disclosure.
Figure 4:
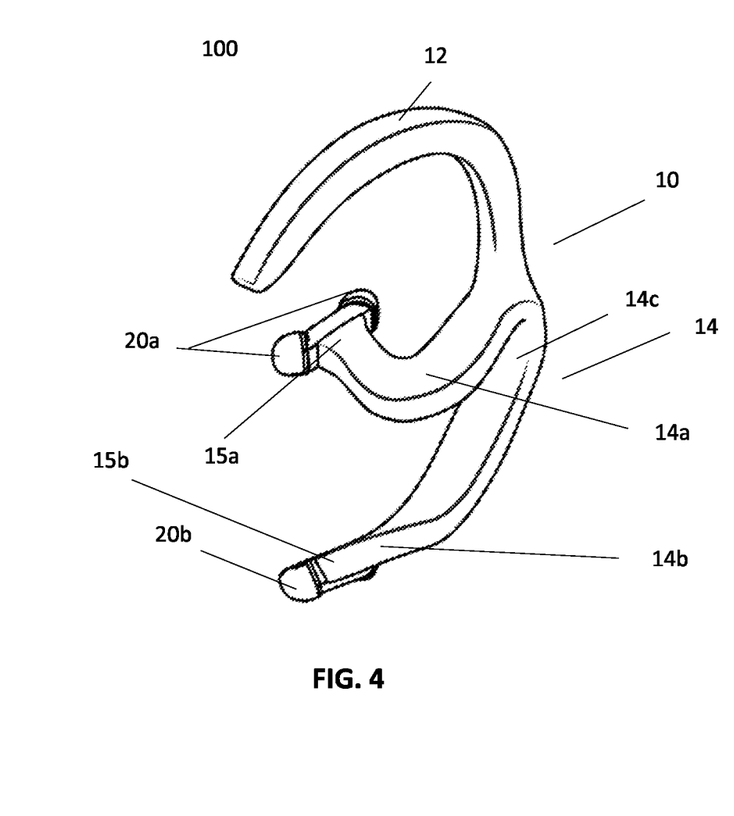
FIG. 4 illustrates another perspective view of an earpiece in accordance with an embodiment of the present disclosure.
Figures 5, 6:
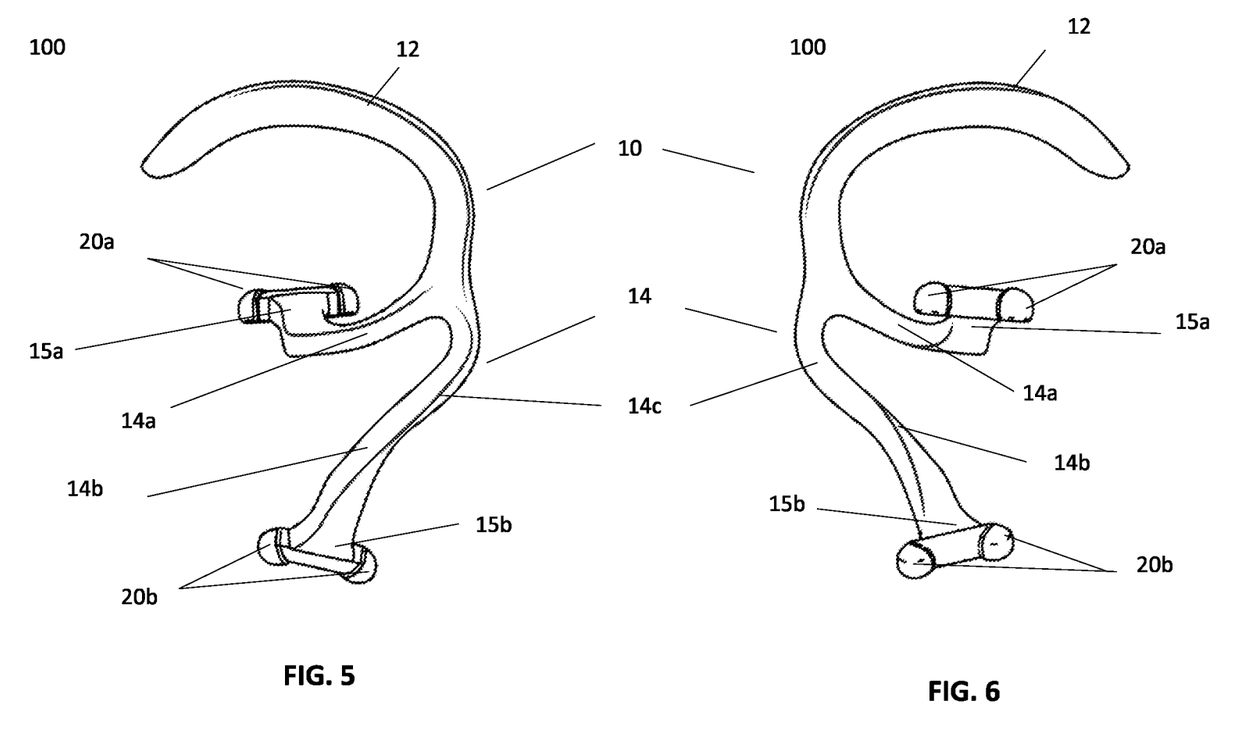
FIG. 5 illustrates a front view of the earpiece of FIGS. 3-4 in accordance with an embodiment of the present disclosure.
FIG. 6 illustrates a rear view of the earpiece of FIGS. 3-5 in accordance with an embodiment of the present disclosure.
Figure 7:
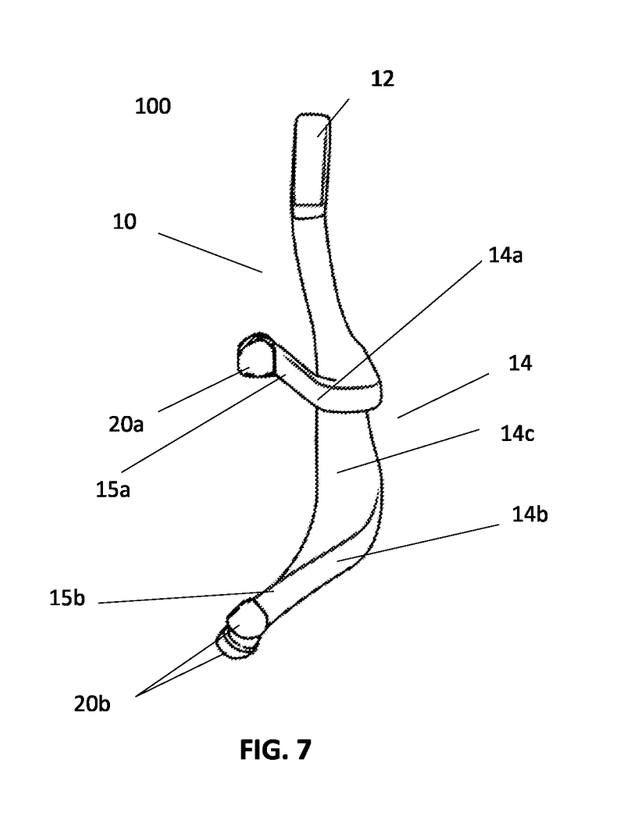
FIG. 7 illustrates a left side view of the earpiece of FIGS. 3-6 in accordance with an embodiment of the present disclosure.
Figure 8:
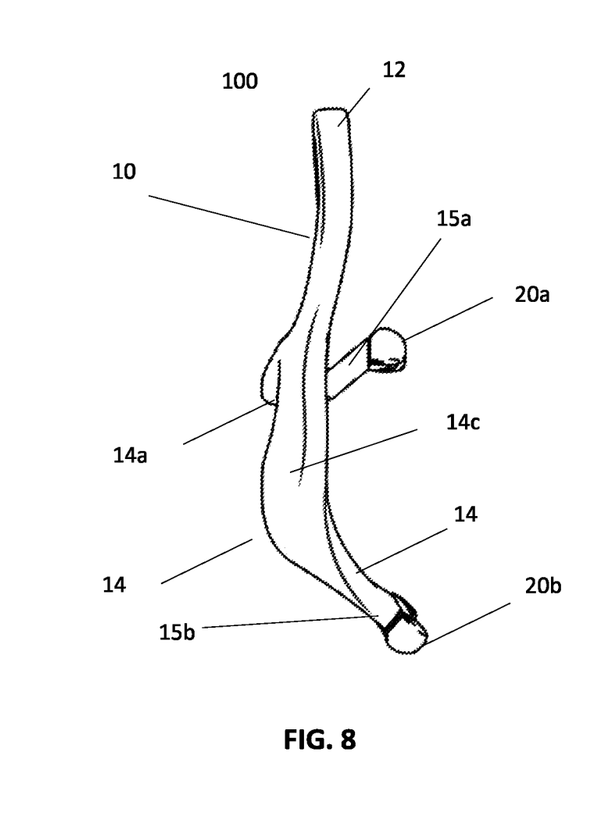
FIG. 8 illustrates a right side view of the earpiece of FIGS. 3-7 in accordance with an embodiment of the present disclosure.

The vagus nerve includes an auricular branch that extends into the user's ear, both the left and right ear. FIG. 1 illustrates exemplary positioning of the auricular branch of the vagus nerve in the user's ear. FIG. 2 illustrates two areas (Area 1, Area 2) of the user's ear where the auricular branch of the vagus nerve is positioned close to the surface of the user's skin.

In view of the multiple organs and systems regulated by the vagus nerve, stimulation of the vagus nerve (vagus nerve stimulation (VNS)) may be used to treat or diagnose various disorders. However, conventional electrodes are not reliably placed in and held in place in the user's ears to provide the desired stimulation. Further, conventional electrodes do not allow for reliable placement of the electrodes in ears of different sizes and shapes.

Accordingly, it would be beneficial to provide an earpiece including one or more electrodes suitable for positioning the one or more electrodes in the user's ear to reliably stimulate the auricular branch of the vagus nerve.

SUMMARY

It is an object of the present disclosure to provide an earpiece including electrodes that are positioned to stimulate the auricular branch of the vagus nerve. In embodiments, the earpiece may include flexible arms that may be adjusted to accommodate ears of different sizes while maintaining desired positioning of the electrodes relative to the vagus nerve.

An earpiece in accordance with an embodiment of the present disclosure includes: a frame including: an over ear element configured to extend over and behind a top of a user's ear to hold the earpiece in place on the user's ear; and a flexible portion positioned below the over ear element and connected to a bottom portion of the over ear element; the flexible portion including: an upper arm including a first electrode positioned at a first free end of the upper arm; a lower arm positioned below the upper arm and including a second electrode positioned at a second free end of the lower arm; and a pivot element connecting a first connected end of the upper arm, opposite the first free end, to a second connected end of the lower arm, opposite the second free end, wherein the pivot element is flexible and resilient such that the upper arm and lower arm flex toward each other when pressure is applied and return to a rest position when pressure is not applied.

In embodiments, the over ear element includes a curved element that extends over the top of the user's ear and a top portion that is received behind the top of the user's ear.

In embodiments, the upper arm is positioned such that the first free end of the upper arm extends adjacent to the second free end of the lower arm with a space provided between the first free end and the second free end.

In embodiments, the pivot element is made of a flexible and resilient material that biases the upper arm and lower arm to the rest position when no pressure is applied.

In embodiments, the first electrode is pressed into a first desired area of an ear in the rest position and the second electrode is pressed into a second desired area of the ear in the rest position.

In embodiments, the first electrode applies voltage to the first desired area and the second electrode applies voltage to the second desired area in the rest position.

In embodiments, the first desired area of the ear and the second desired area of the ear correspond to a position of an auricular branch of a vagus nerve of the user.

In embodiments, the first electrode includes a first pair of electrodes spaced apart at a first desired distance such that the first pair of electrodes apply voltage to the first desired area of the ear.

In embodiments, the second electrode includes a second pair of electrodes spaced apart at a second desired distance such that the second pair of electrodes apply voltage to the second desired area of the ear.

In embodiments, the earpiece includes a voltage source provided on the frame and connected to the first pair of electrodes and the second pair of electrodes.

In embodiments, the earpiece includes a controller operably connected to the voltage source and operable to provide control signals to the voltage source to provide a desired voltage to the first pair of electrodes and the second pair of electrodes.

In embodiments, the controller is integrated into the voltage source.

In embodiments, the controller is wirelessly connected to the voltage source.

In embodiments, the earpiece includes an input element operably connected to the controller to provide input to the controller, wherein the control signals are based on the input.

In embodiments, the earpiece includes a voltage source provided on the frame and electrically connected to the first electrode and the second electrode.

In embodiments, the earpiece includes a controller operably connected to the voltage source and operable to provide control signals to the voltage source to provide a desired voltage to the first electrode and the second electrode.

In embodiments, the controller is integrated into the voltage source.

In embodiments, the controller is wirelessly connected to the voltage source.

In embodiments, the earpiece includes an input element operably connected to the controller to provide input to the controller, wherein the control signals are based on the input.

BRIEF DESCRIPTION OF THE DRAWINGS

The above and related objects, features and advantages of the present disclosure will be more fully understood by reference to the following, detailed description of the preferred, albeit illustrative, embodiments of the present invention when taken in conjunction with the accompanying figures, wherein.

DETAILED DESCRIPTION OF THE EXEMPLARY EMBODIMENTS

FIGS. 3-8 illustrate an earpiece 100 that includes a frame 10 including an over ear portion 12 and a flexible portion 14. In embodiments, the over ear portion 12 is configured to curve upward and extend around a top portion of the user's ear such that a free end thereof is positioned behind the user's ear to hold the earpiece 100 in place on the user's ear. This is generally illustrated in FIGS. 10, 14A, 14B and 14C for example, where the over ear portion 12 extends over the top portion of the user's ear and the end is received behind the top of the user's ear.

Figure 10:
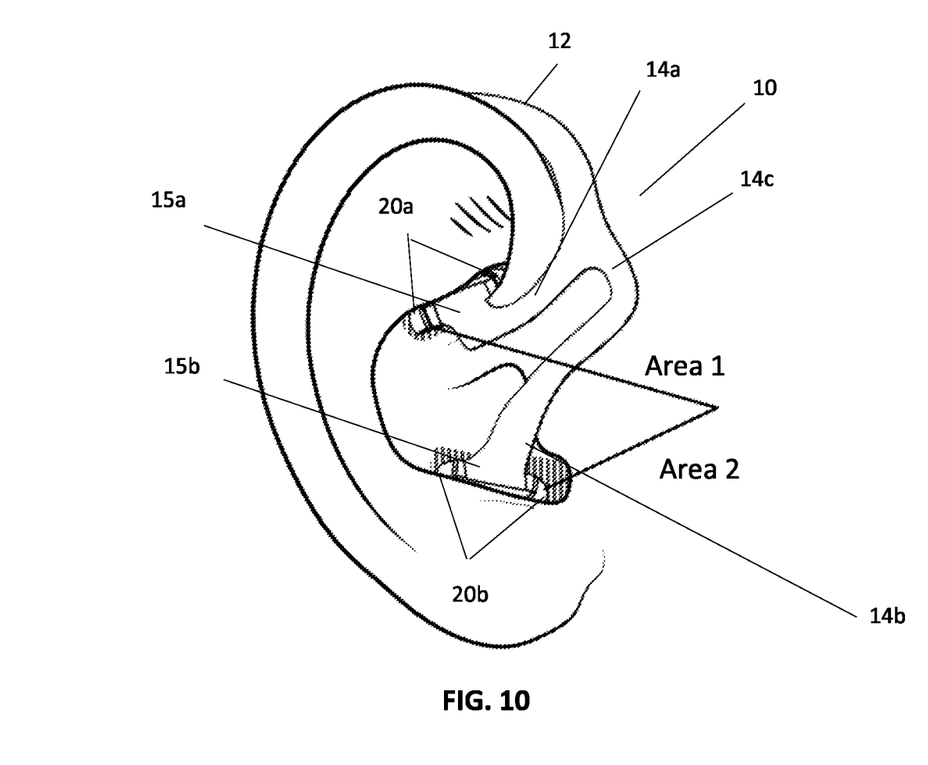
FIG. 10 illustrates the earpiece of FIG. 9 with the upper and lower arms released to return to their original position to contact the user's ear in accordance with an embodiment of the present disclosure.

In embodiments, the lower flexible portion 14 may include an upper arm 14a including at least a first electrode 20a. In embodiments, the first electrode 20a may include a first pair of electrodes 20a spaced from each other by a predetermined distance. In embodiments, the predetermined space may be between 5 mm and 15 mm. In embodiments, the predetermined space may be larger or smaller. In embodiments, the electrode(s) 20a may be positioned such that they are aligned with Area 1 (see FIG. 1) of the user's ear when the earpiece 100 is applied to the user's ear, as can be seen in FIG. 10 as well. In embodiments, the electrode(s) 20a are positioned in Area 1 to provide transcutaneous stimulation of the auricular branch of the vagus nerve.

In embodiments, the lower flexible portion 14 may include a lower arm 14b including a second of electrode 20b. In embodiments, the second electrode 20b may be a second pair of electrodes 20b spaced from each other by a second predetermined distance. In embodiments, the second predetermined space may be between 5 mm and 15 mm. In embodiments, the second predetermined space may be larger or smaller. In embodiments, the electrode(s) 20b may be positioned such that they are aligned with Area 2 (see FIG. 10, for example) of the user's ear when the frame 10 of the earpiece 100 is applied to the user's ear. In embodiments, the electrode(s) 20b are positioned in Area 2 to provide transcutaneous stimulation of the auricular branch of the vagus nerve.

Figure 9:
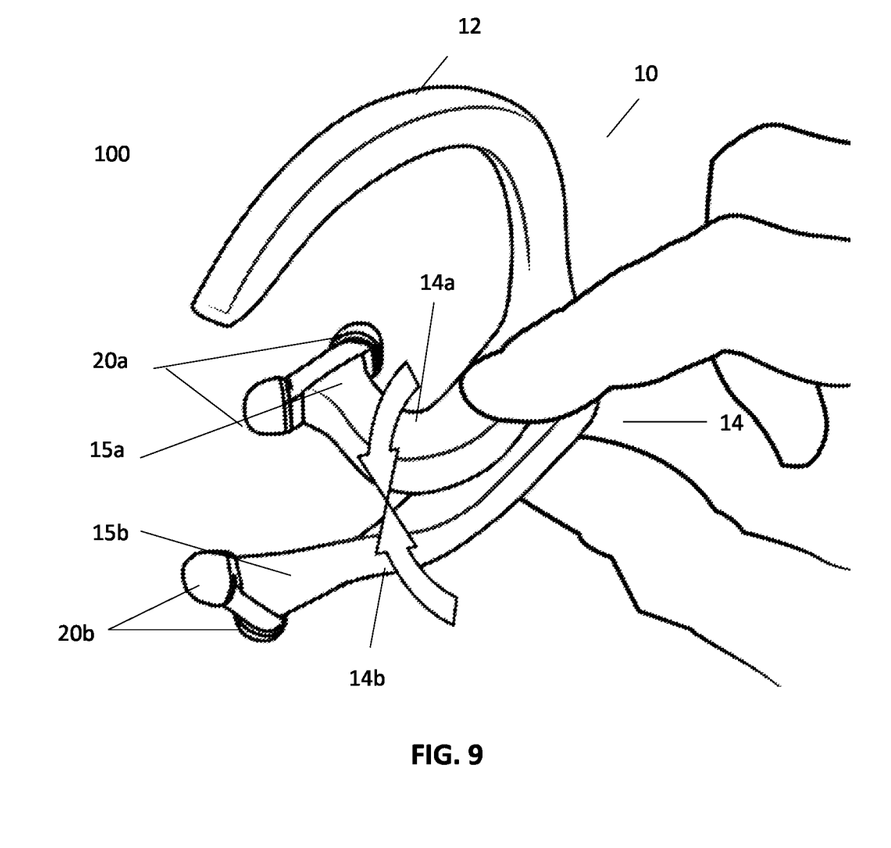
FIG. 9 illustrates the earpiece of FIGS. 3-8 with the upper and lower arms thereof flexed toward each other in accordance with an embodiment of the present disclosure.

In embodiments, the upper arm 14a and the lower arm 14b may be connected to each other via a pivot section 14c. In embodiments, at least the pivot section 14c may be made of a flexible and resilient material such that the upper arm 14a and the lower arm 14b are flexible relative to each other. In embodiments, the pivot section 14c may be made of thermoplastic polyurethane (TPU), polyvinyl chloride (PVC), or polypropylene, to name a few. In embodiments, the upper arm 14a and the lower arm 14b may be made of the same material as the pivot section 14c. In embodiments, the upper arm 14a and/or the lower arm 14b may be made of a different material than the pivot section 14c or may be combinations of TPU, PVC or polypropylene. In embodiments, any suitable material may be used for the upper arm 14a and lower arm 14b. FIG. 9 illustrates an example of a user pressing the upper arm 14a and the lower arm 14b toward each other. As can be seen in FIG. 9, the upper arm 14a and the lower arm 14b flex toward each other via the flexible hinge portion 14c when the user applies pressure to the upper arm 14a and the lower arm 14b. The arrows in FIG. 9 illustrate the direction of flex of the arms 14a, 14b. When pressure is removed, the upper arm and lower arm return to a rest position, as generally illustrated in FIGS. 3-8 and 10. In embodiments, the upper arm 14a and lower arm 14b extend adjacent to each other and the pivot section 14c connects the upper arm and the lower arm on one side thereof while the opposite ends 15a, 15b are free ends. The pivot section 14c connects the upper arm 14a and lower arm 14b on first and second connected ends, respectively such that a space is provided between the free ends 15a, 15b thereof to allow the arms to move when they flex.

In FIG. 10, in embodiments, once the arms 14a, 14b are flexed toward each other, the electrodes 20a, 20b may be positioned in the user's ear such that the electrode(s) 20a are positioned in the Area 1 and the electrode(s) 20b are positioned in the Area 2. In embodiments, when the user releases the pressure on the arms 14a, 14b, the resilient arms substantially return to the rest position to press the electrodes 20a, 20b against the user's ear in Area 1 and Area 2, respectively.

Figure 11:
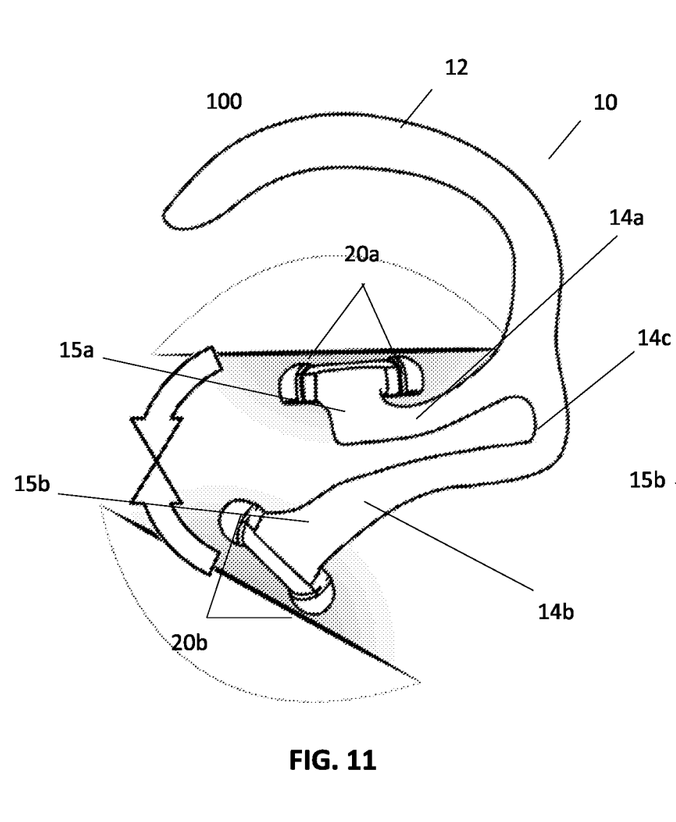
FIG. 11 illustrates the earpiece of FIG. 3-10 with the upper and lower arms flexed inward and positioned in the user's ear in accordance with an embodiment of the present disclosure.
Figure 12:
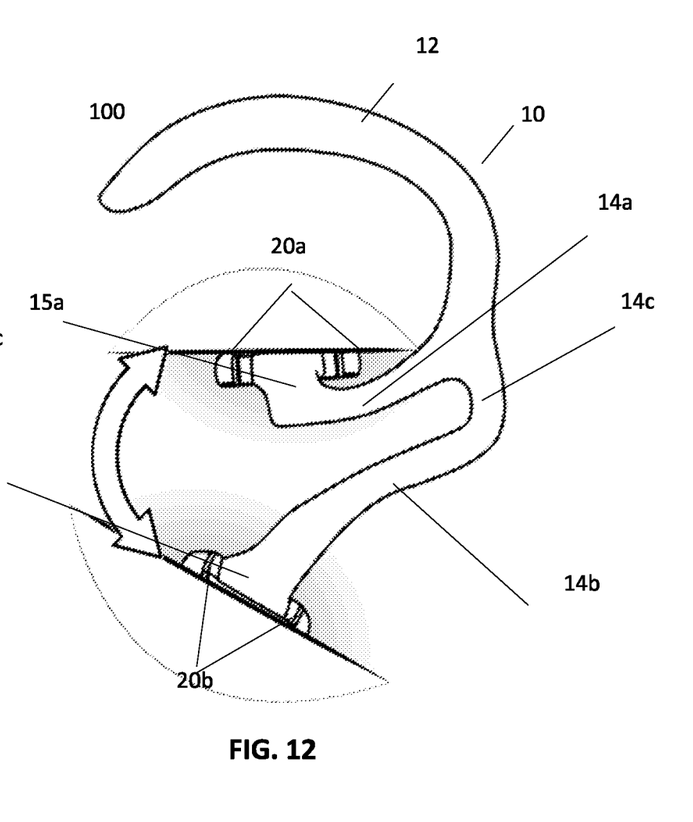
FIG. 12 illustrates the earpiece of FIG. 11 with the upper and lower arms released to push the electrodes against the user's ear in accordance with an embodiment of the present disclosure.

In embodiments, FIG. 11 shows the arms 14a, 14b flexed inward such that they can be inserted into the user's ear. In embodiments, once the pressure is released, the arms expand back to the rest position such that the electrodes 20a, 20b are pressed into contact with the user's ear as illustrated in FIG. 12.

Figure 13A:
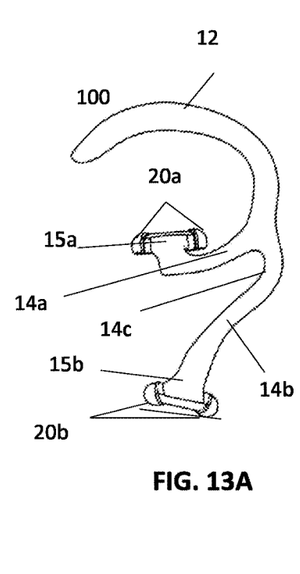
FIGS. 13A-13E illustrate examples of earpieces of difference sizes in accordance with an embodiment of the present disclosure.

FIGS. 13A-13E illustrate examples of earpieces 100 of different sizes that may be used with ears of different sizes. FIG. 13A, for example, is suitable for use with a relatively large ear while FIGS. 13B, 13C, 13D and 13E are suitable for use with progressively smaller ears, respectively. As can be seen in FIGS. 13A-13E, in embodiments, the earpieces 100 of different sizes may have different spacing between the arms 14a and 14b with larger spacing being used for larger ears and smaller spacing suitable for use with smaller ear sizes.

Figure 13B:
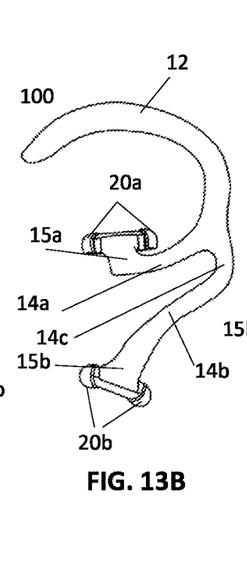
Figures 13C, 13D:
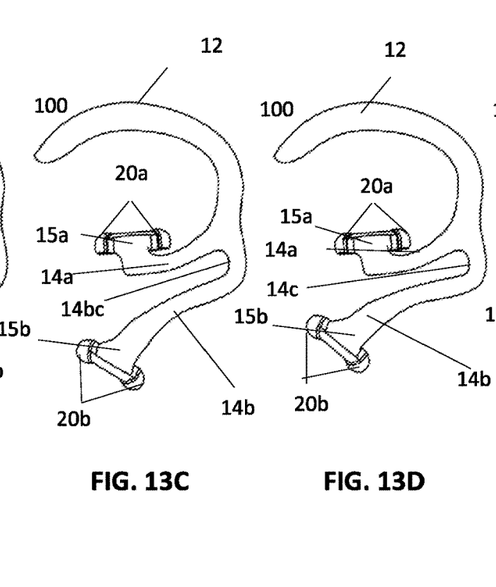
Figure 13E:
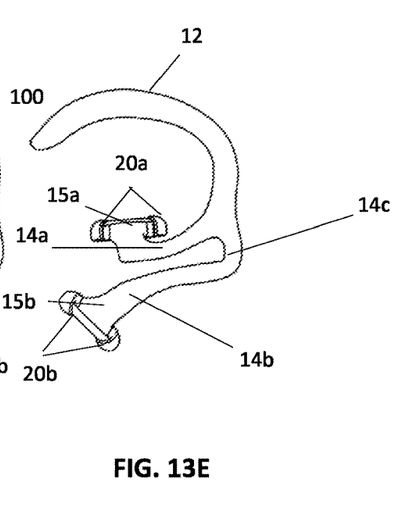
Figure 14A:
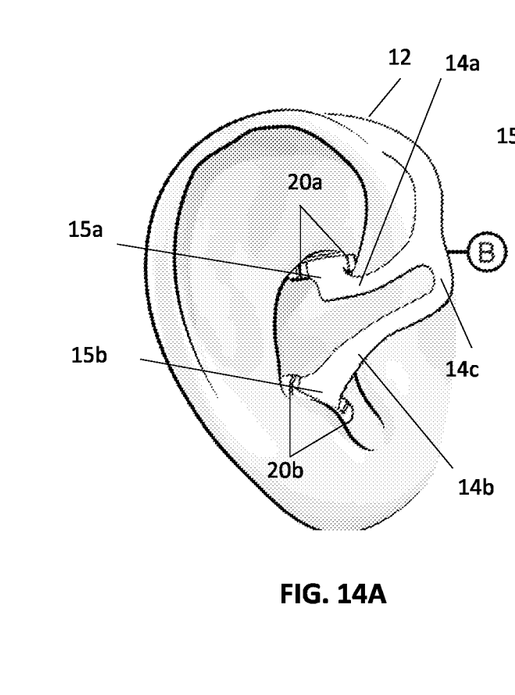
FIG. 14A illustrates the earpiece of FIG. 13B mounted in a user's ear in accordance with an embodiment of the present disclosure.
Figure 14B:
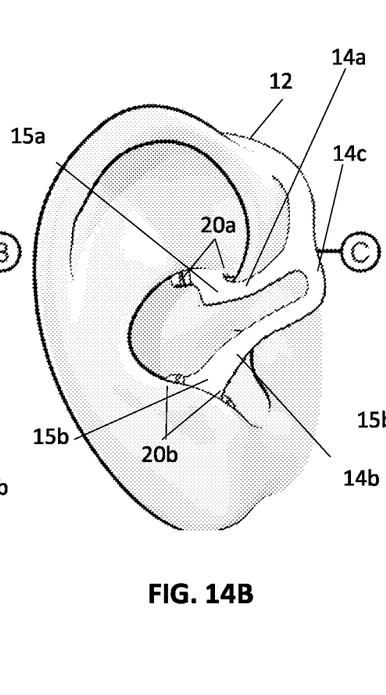
FIG. 14B illustrates the earpiece of FIG. 13C mounted in a user's ear in accordance with an embodiment of the present disclosure.
Figure 14C:
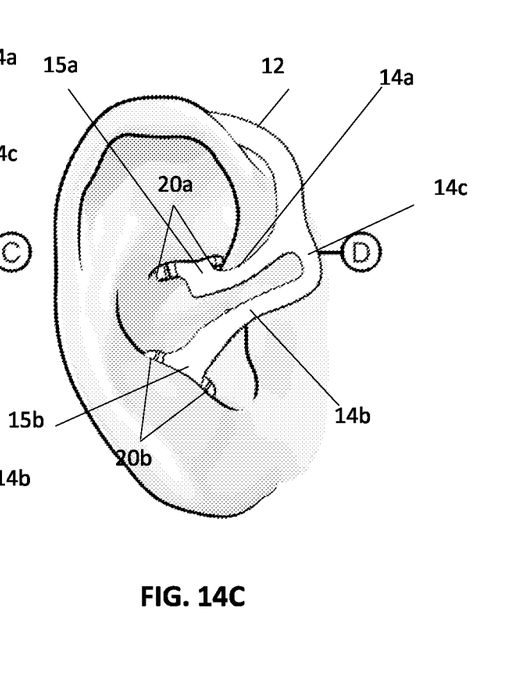
FIG. 14C illustrates the earpiece of FIG. 13D mounted in a user's ear in accordance with an embodiment of the present disclosure.

FIG. 14A illustrates the earpiece 100 of FIG. 13B positioned in a user's ear in accordance with an embodiment of the present disclosure. FIG. 14B illustrates the earpiece of FIG. 13C positioned in a user's ear and FIG. 14C illustrates the earpiece of FIG. 13D in a user's ear in accordance with an embodiment of the present disclosure.

Figure 15:
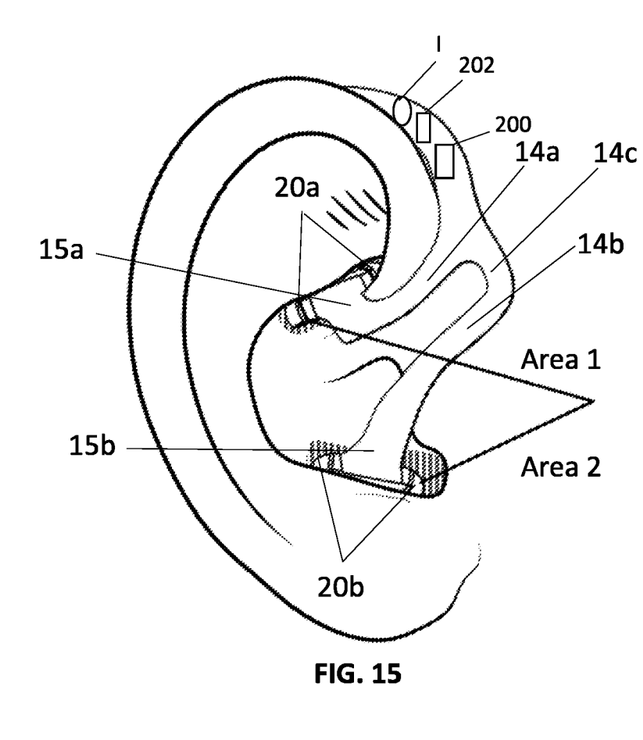
FIG. 15 illustrates the earpiece of FIGS. 3-10 including a voltage source controlled by a controller and an input element in accordance with an embodiment of the present disclosure.
Figure 16:
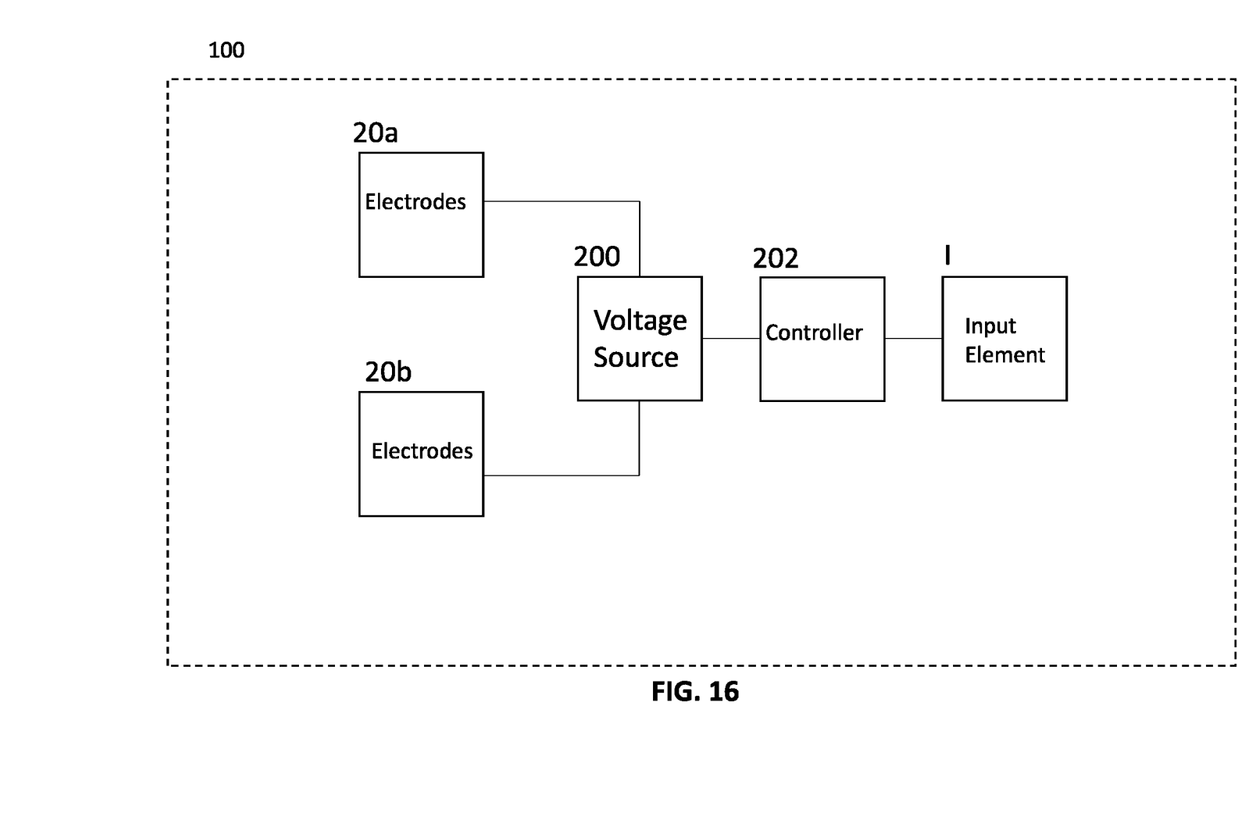
FIG. 16 illustrates a block diagram of an earpiece showing the connection between a voltage source and the electrodes as well as the connection between the controller, input device and voltage source in accordance with an embodiment of the present disclosure.

In embodiments, the electrodes 20a, 20b may be used to apply a transcutaneous voltage to the auricular branch of the vagus nerve. In embodiments, the voltage may be provided in the form of a waveform configured to provide treatment or to aid in diagnosing medical conditions. In embodiments, the electrodes 20a, 20b may be connected to a voltage source 200 (see FIGS. 15-16) via a wire connection and or a conductive path provided in the arms 14a, 14b. In embodiments, a voltage source 200 may be included in or on the earpiece 100 (See FIG. 15, for example) which may be connected to the electrodes 20a, 20b as indicated in the block diagram of FIG. 16, for example. In embodiments, the voltage source 200 may be a battery, rechargeable battery, transformer, capacitor, or any other suitable voltage source. In embodiments, the voltage source 200 may be controlled by a controller 202 (see FIGS. 15-16) positioned on or in the frame 10 of the earpiece 100 which may provide control signals to the voltage source to provide a desired voltage. In embodiments, the voltage from the voltage source 200 may be provided to the electrodes 20a, 20b via the controller 202. In embodiments, the controller 202 may be integrated into the voltage source 200. In embodiments, the controller 202 may control the voltage source 200 based on input provided at the earpiece 100, via an input element I (see FIGS. 15-16), for example. In embodiments, the controller 202 may control the voltage source 200 based on input provided wirelessly by a mobile electronic device such as a smart phone, tablet or laptop computer, to name a few. In embodiments, the controller 202 and voltage source 200 may be provided remotely from the earpiece 100 and the voltage or waveform may be provided to the earpiece via a wire or wirelessly. In embodiments, the voltage source 200 may power the controller 202. In embodiments, the controller 202 may be a microcontroller or any other suitable logic element.

Although the present invention has been described in relation to particular embodiments thereof, many other variations and modifications and other uses will become apparent to those skilled in the art. It is preferred, therefore, that the present invention be limited not by the specific disclosure herein.

What is claimed is:

1. An earpiece comprises:
a frame including:
an over ear element configured to extend over and behind a top of a user's ear to hold the earpiece in place on the user's ear; and
a flexible portion positioned below the over ear element and connected to a bottom portion of the over ear element;
the flexible portion including:
an upper arm including a first electrode positioned at a first free end of the upper arm;
a lower arm positioned below the upper arm and including a second electrode positioned at a second free end of the lower arm; and
a pivot element connecting a first connected end of the upper arm, opposite the first free end, to a second connected end of the lower arm, opposite the second free end,
wherein the pivot element is flexible and resilient such that the upper arm and lower arm flex toward each other when pressure is applied and return to a rest position when pressure is not applied.

2. The earpiece of claim 1, wherein the over ear element includes a curved element that extends over the top of the user's ear and a top portion that is received behind the top of the user's ear.

3. The earpiece of claim 1, wherein the upper arm is positioned such that the first free end of the upper arm extends adjacent to the second free end of the lower arm with a space provided between the first free end and the second free end.

4. The earpiece of claim 1, wherein the pivot element is made of a flexible and resilient material that biases the upper arm and lower arm to the rest position when no pressure is applied.

5. The earpiece of claim 1, wherein the first electrode is pressed into a first desired area of an ear in the rest position and the second electrode is pressed into a second desired area of the ear in the rest position.

6. The earpiece of claim 5, wherein the first electrode applies voltage to the first desired area and the second electrode applies voltage to the second desired area in the rest position.

7. The earpiece of claim 5, wherein the first desired area of the ear and the second desired area of the ear correspond to a position of an auricular branch of a vagus nerve of the user.

8. The earpiece of claim 5, wherein the first electrode includes a first pair of electrodes spaced apart at a first desired distance such that the first pair of electrodes apply voltage to the first desired area of the ear.

9. The earpiece of claim 8, wherein the second electrode includes a second pair of electrodes spaced apart at a second desired distance such that the second pair of electrodes apply voltage to the second desired area of the ear.

10. The earpiece of claim 9, further comprising a voltage source provided on the frame and connected to the first pair of electrodes and the second pair of electrodes.

11. The earpiece of claim 10, further comprising a controller operably connected to the voltage source and operable to provide control signals to the voltage source to provide a desired voltage to the first pair of electrodes and the second pair of electrodes.

12. The earpiece of claim 11, wherein the controller is integrated into the voltage source.

13. The earpiece of claim 11, wherein the controller is wirelessly connected to the voltage source.

14. The earpiece of claim 11, further comprising an input element operably connected to the controller to provide input to the controller, wherein the control signals are based on the input.

15. The earpiece of claim 6, further comprising a voltage source provided on the frame and electrically connected to the first electrode and the second electrode.

16. The earpiece of claim 15, further comprising a controller operably connected to the voltage source and operable to provide control signals to the voltage source to provide a desired voltage to the first electrode and the second electrode.

17. The earpiece of claim 16, wherein the controller is integrated into the voltage source.

18. The earpiece of claim 16, wherein the controller is wirelessly connected to the voltage source.

19. The earpiece of claim 16, further comprising an input element operably connected to the controller to provide input to the controller, wherein the control signals are based on the input.

* * * * *